US008414295B2

United States Patent
Wu et al.

(10) Patent No.: US 8,414,295 B2
(45) Date of Patent: Apr. 9, 2013

(54) NON-CONTACT APPARATUS AND METHOD FOR STABILITY ASSESSMENT OF DENTAL IMPLANT

(75) Inventors: Wen-Hong Wu, Kaohsiung (TW); Keng-Liang Ou, Kaohsiung (TW); Kuo-Cheng Huang, Hsinchu (TW)

(73) Assignee: National Applied Research Laboratories, Taipei (TW)

( * ) Notice: Subject to any disclaimer, the term of this patent is extended or adjusted under 35 U.S.C. 154(b) by 379 days.

(21) Appl. No.: 12/244,982

(22) Filed: Oct. 3, 2008

(65) Prior Publication Data
US 2009/0092945 A1 Apr. 9, 2009

(30) Foreign Application Priority Data
Oct. 5, 2007 (TW) .............................. 96137607 A

(51) Int. Cl.
*A51C 8/00* (2006.01)
*A61C 8/00* (2006.01)
(52) U.S. Cl. ........................... 433/173; 433/72; 600/552
(58) Field of Classification Search .................. 433/72, 433/215, 172–174; 600/589, 590, 552, 553; 33/513
See application file for complete search history.

(56) References Cited

U.S. PATENT DOCUMENTS

| 5,049,073 | A | | 9/1991 | Lauks |
| 5,392,779 | A | * | 2/1995 | Meredith et al. ............. 600/437 |
| 5,531,597 | A | * | 7/1996 | Foulkes et al. ................ 433/119 |
| 6,712,778 | B1 | * | 3/2004 | Jeffcoat et al. ................ 600/590 |
| 6,918,763 | B2 | * | 7/2005 | Huang et al. .................... 433/72 |
| 2003/0022129 | A1 | * | 1/2003 | Rahman et al. .............. 433/119 |

FOREIGN PATENT DOCUMENTS

| CN | 1736342 | 2/2006 |
| TW | 200631556 | 9/2006 |

OTHER PUBLICATIONS

Office Action and Search Report from corresponding application No. TW096137607, dated Sep. 7, 2010.
Taiwanese Office Action, Application No. TW096137607, issued Nov. 14, 2012.

\* cited by examiner

*Primary Examiner* — Cris L Rodriguez
*Assistant Examiner* — Eric Rosen
(74) *Attorney, Agent, or Firm* — Volpe and Koenig, P.C.

(57) ABSTRACT

A non-contact apparatus for a stability assessment of a dental implant is provided. The non-contact apparatus includes a triggering device and a dental implant containing a root body and an impact generating device, wherein the root body has a cavity, the impact generating device is located in the cavity, and the triggering device provides a non-contact impetus for triggering the impact generating device.

14 Claims, 4 Drawing Sheets

NON-CONTACT APPARATUS AND METHOD FOR STABILITY ASSESSMENT OF DENTAL IMPLANT

FIELD OF THE INVENTION

The present invention relates to an apparatus and a method for stability assessment of dental implant, and more particularly to a non-contact apparatus and a non-contact method for stability assessment of dental implant.

BACKGROUND OF THE INVENTION

Current dental implantations can be divided into a one-stage system and a two-stage system based on the designs of the dental implants and the corresponding surgery operations thereof. After a dental implant is implanted in an alveolus bone, a direct and rigid contact will be formed between the dental implant and the neo-bone during the osteo-concrescence process, and such a process is the so-called osseointegration, which provides well stability between the dental implant and the bone tissue. Generally speaking, it takes about six months for the alveolus bone of a supramaxillary to achieve the expected level of osseointegration, whereas it takes about three to four months for a submaxillary. In the one-stage dental implant system, a part of the dental implant is located at the outside of the gum, and an artificial crown will be mounted on the dental implant after the osseointegration. On the other hand, in the two-stage dental implant system, the whole dental implant is covered in the gum, and the gum will be incised for mounting the artificial crown after the osseointegration. Because the dental implant is covered in the gum during the osseointegration, the probability of infections and the external stimulus will be reduced, so that the dental implant can be integrated with the alveolus bone more stably.

The stability of the dental implant is a key factor in a successful dental implantation. The better the osseointegration is, the higher density the alveolus bone will have, and the higher stability the dental implant will have, such that the success rate of the regional dental implantation will be higher. Therefore, the stability assessment of the dental implant is a key step in the dental implantation. Presently, common measurements of the stability assessment of dental implants include X-ray image measurements and resonance frequency measurements. However, there is a big difficulty in quantity determination when doing the X-ray image measurements, where the bone variation less than 30% can not be detected thereby. Moreover, angles of taking X-ray images will affect the accuracy of readings; X-ray also harms human bodies, and the technicians of operating X-ray machines must be well-trained. Besides, X-ray imaging instruments are very expensive. Compared with X-ray image measurements, resonance frequency measurements do not have the mentioned limitations.

Currently, in the clinical practice, one of the resonance frequency measurements for assessing the stability of dental implants is the impulse response method, where a constant external impetus is provided to the dental implant using a hammer to directly impact the dental implant. A vibration response of the dental implant is received by a microphone and provided for frequency spectrum analysis, so as to obtain the resonant frequency of the dental implant and analyze the conditions of the implant/alveolus interface. The higher resonant frequency represents the better stability of the dental implant. Nevertheless, such an impulse response method only fits the one-stage system. Because in the two-stage system, the dental implant is covered in the gum and can not be impacted by the hammer to measure the stability thereof.

From the above description, it is necessary to provide a method to measure the resonant frequency of the dental implant without any contact, and such a method is suitable for both of the one-stage and two-stage dental implant systems. In addition, this non-contact method avoids the inconveniences of the conventional resonance frequency measurements, where a direct contact of external impacts is necessary. This non-contact method also decreases the psychological uncomfortableness of patients.

In order to overcome the drawbacks in the prior art, a non-contact apparatus and a non-contact method for stability assessment of dental implant are provided. The particular design in the present invention not only solves the problems described above, but also is easy to be implemented. Thus, the invention has the utility for the industry.

SUMMARY OF THE INVENTION

In accordance with one aspect of the present invention, a non-contact apparatus for stability assessment of dental implant and the method of using the same are provided, where the resonance frequency measurements are used to analyze the stability of a dental implant. A non-contact impetus is provided to a dental implant for generating a vibration thereof, and thus the present invention can be applied in a two-stage dental implant system. The present invention overcomes the drawbacks of the conventional resonance frequency measurements, which are only applied in a one-stage dental implant system, and thus provides a more precise diagnosis in a dental implantation.

In accordance with another aspect of the present invention, a non-contact apparatus for a stability assessment of a dental implant is provided. The non-contact apparatus includes a triggering device and a dental implant containing a root body and an impact generating device, wherein the root body has a cavity in which the impact generating device is located, and the triggering device provides a non-contact impetus for triggering the impact generating device.

Preferably, the non-contact apparatus further includes a receiving device, wherein the non-contact impetus triggers the impact generating device to make the dental implant generate a vibration response, and the receiving device receives the vibration response.

Preferably, the receiving device is a microphone.

Preferably, the non-contact apparatus further includes an analyzing device coupled to the receiving device and analyzing the vibration response received by the receiving device.

Preferably, the analyzing device is a computer.

Preferably, the cavity has an opening, and the dental implant further comprises a cover covering the opening.

Preferably, the dental implant is implanted at an alveolus bone covered by a gum, and the opening and the cover are located in one of an outside of the gum and an inside of the gum.

Preferably, the impact generating device is a hammer having a stick connected to an inside surface of one of the cover and the root body.

Preferably, the impact generating device is a piece placed in the cavity.

Preferably, the impact generating device is made of a material with a magnetic permeability.

Preferably, the material is one selected from a group consisting of an iron, a cobalt, a nickel, a gadolinium and a combination thereof.

Preferably, the triggering device is a magnetic field generating device for generating one of a periodical magnetic field and an impulse magnetic field.

In accordance with a further aspect of the present invention, a non-contact method for a stability assessment of a dental implant is provided. The non-contact method includes steps of providing a non-contact impetus to a dental implant, generating a vibration response by the dental implant in response to the non-contact impetus, and receiving and analyzing the vibration response.

Preferably, the step of receiving and analyzing the vibration response is to obtain a resonant frequency of the dental implant.

Preferably, the non-contact impetus triggers an impact generating device in the dental implant to make the dental implant generate the vibration response.

Preferably, the non-contact method is applied in one of a one-stage dental implant system and a two-stage dental implant system.

Preferably, the non-contact impetus is one of an impulse magnetic field and a periodical magnetic field.

In accordance with further another aspect of the present invention, a dental implant is provided. The dental implant includes a root body and an impact generating device located in the root body.

Preferably, the root body has a cavity with an opening, and the dental implant further comprises a cover covering the opening.

Preferably, the impact generating device is one of a hammer and an impacting piece, wherein the hammer has a stick connected to an inside surface of one of the cover and the root body, and the impacting piece is placed in the cavity.

Additional objects and advantages of the invention will be set forth in the following descriptions with reference to the accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

Figure 1:
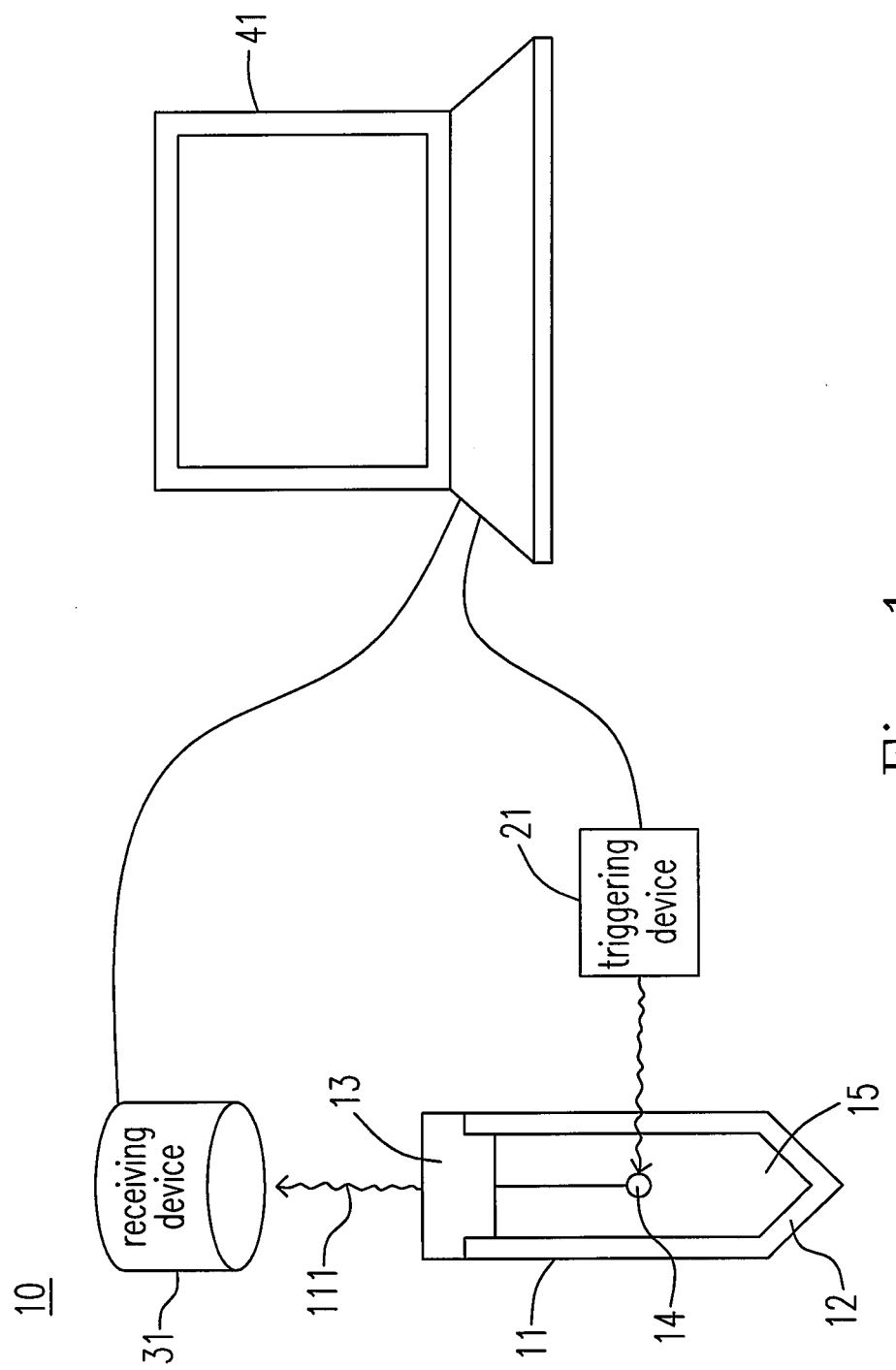
FIG. 1 is a schematic diagram of the non-contact apparatus for a stability assessment of a dental implant according to a preferred embodiment in the present invention.

Please refer to FIG. 1, which shows a schematic diagram of the non-contact apparatus for a stability assessment of a dental implant according to a preferred embodiment in the present invention. The non-contact apparatus 10 includes a dental implant 11, a triggering device 21, a receiving device 31, and an analyzing device 41 coupled to the receiving device 31. The dental implant 11 includes a cover 13, a root body 12 having a cavity 15, and an impact generating device 14 located in the cavity 15.

As shown in FIG. 1, the triggering device 21 triggers the impact generating device 14 to make the dental implant 11 vibrate and generate a vibration response 111. The vibration response 111 is received by the receiving device 31 and transmitted to the analyzing device 41 to be analyzed, so as to obtain a resonant frequency of the dental implant 11, wherein the receiving device 31 can be a microphone, and the analyzing device 41 can be a computer. Besides, the triggering device 21 can be a separate device, or can be coupled to the analyzing device 41 and controlled by the analyzing device 41 as shown in FIG. 1.

Figure 2:
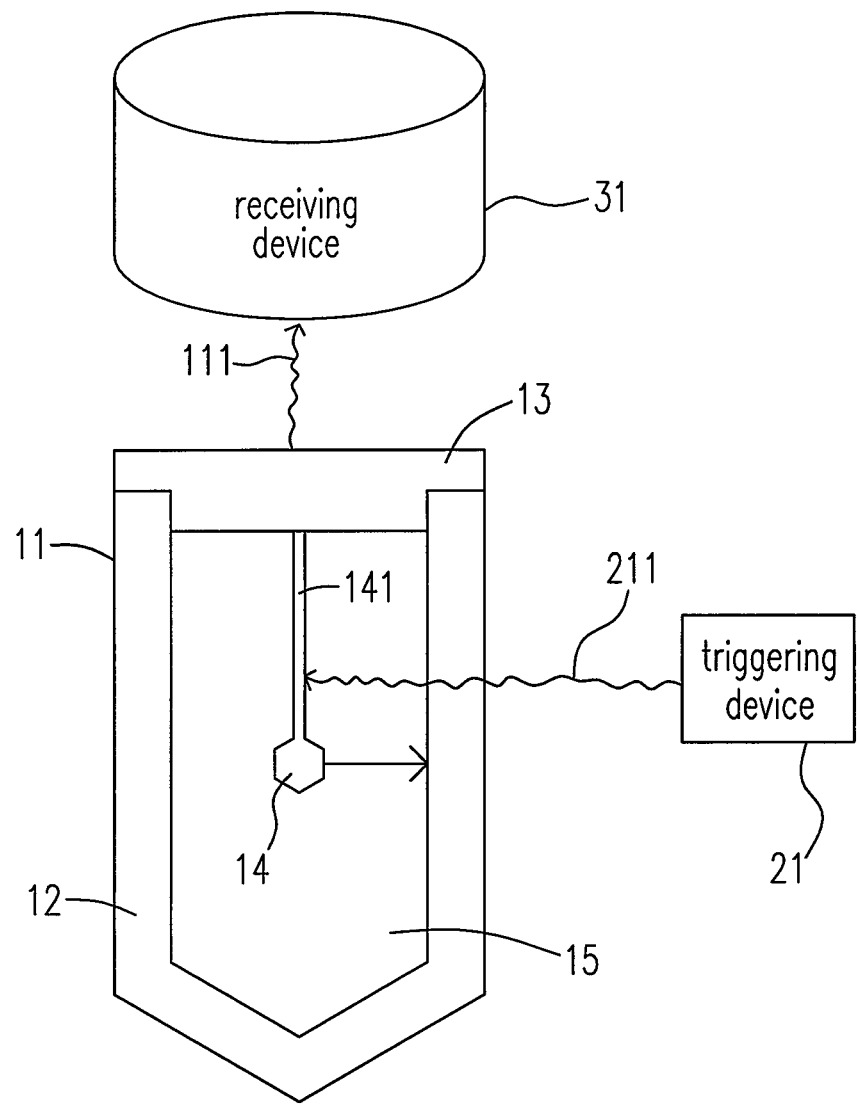
FIG. 2 is a schematic diagram showing the non-contact method for a stability assessment of a dental implant according to a preferred embodiment in the present invention.

Please refer to FIG. 2, which is a schematic diagram showing the non-contact method for a stability assessment of a dental implant according to a preferred embodiment in the present invention. The triggering device 21 provides a non-contact impetus 211 to the impact generating device 14, where the impact generating device 14 impacts the root body 12 when once triggered, so that the dental implant 11 vibrates and generates the vibration response 111, and the vibration response 111 is received by the receiving device 31 and analyzed by the analyzing device 41.

When the triggering device 21 is a coil for generating an impulse magnetic field, and the non-contact impetus 211 is the impulse magnetic field, the impact device 14 can be made of the material with magnetic permeability selected from a group consisting of iron, cobalt, nickel, gadolinium, and a combination thereof. Once the impulse magnetic field affects the impact generating device 14 and makes it oscillate and impact the root body 12, the dental implant 11 will generate the vibration response 111, which will be received by the receiving device 31. On the other hand, when the triggering device 21 is a magnetic field generating device for generating a periodical magnetic field, and the non-contact impetus 211 is the periodical magnetic field, the material of the impact generating device 14 is not limited to the mentioned materials with magnetic permeability. When the triggering device 21 generates the periodical magnetic field with the frequency the same as the known resonant frequency of the impact generating device 14, the impact device 14 will oscillate violently and impact the root body 12, such that the dental implant 11 will generate the vibration response 111, which will be received by the receiving device 31.

Figure 3A:
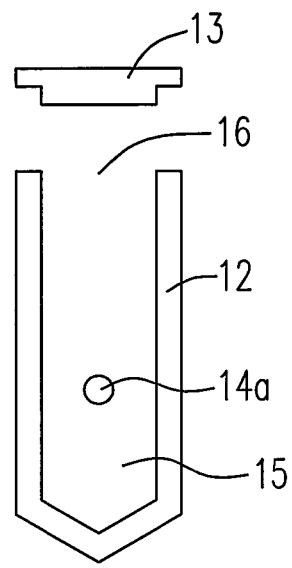
FIG. 3(a) is a schematic diagram of the dental implant according to a preferred embodiment in the present invention.
Figure 3B:
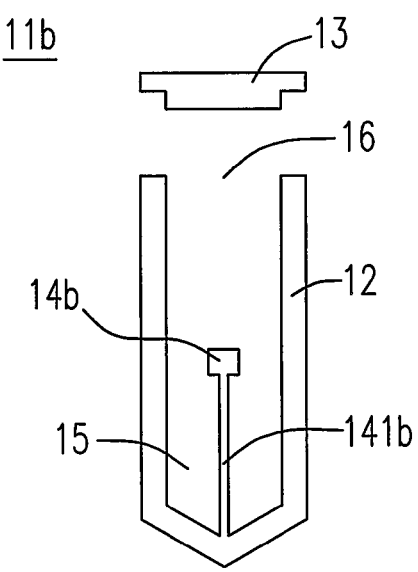
FIG. 3(b) is a schematic diagram of the dental implant according to another preferred embodiment in the present invention.

Please refer to FIG. 3(a), which is a schematic diagram showing the dental implant according to a preferred embodiment in the present invention, wherein the dental implant 11a includes a root body 12 having a cavity 15 and an opening 16, a cover 13 covering the opening 16, and an impact generating device 14a. As shown in FIG. 3(a), the impact generating device 14a is a separate piece placed in the cavity 15 of the root body 12, and can be triggered by a triggering device (not shown) and further impact the root body 12. Please refer to FIG. 3(b), which is a schematic diagram showing the dental implant according to another preferred embodiment in the present invention. Similarly, the dental implant 11b includes a root body 12 having a cavity 15 and an opening 16, a cover 13 covering the opening 16, and an impact generating device 14b, wherein the impact generating device 14b is a hammer located in the cavity 15 of the root body 12, and has a stick 141 connected to an inside surface of the root body 12. Furthermore, as shown in FIG. 2, the impact generating device 14 can be a hammer located in the cavity 15 of the root body 12, and the hammer has a stick 141 connected to an inside surface of the cover 13. Thus, the impact generating device 14 can be taken out when the cover 13 is removed.

Figure 4A:
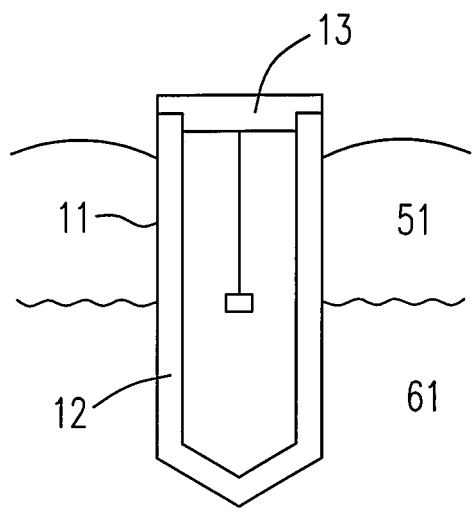
FIG. 4(a) is a schematic diagram showing the dental implant implanted in an alveolus bone according to a preferred embodiment in the present invention.
Figure 4B:
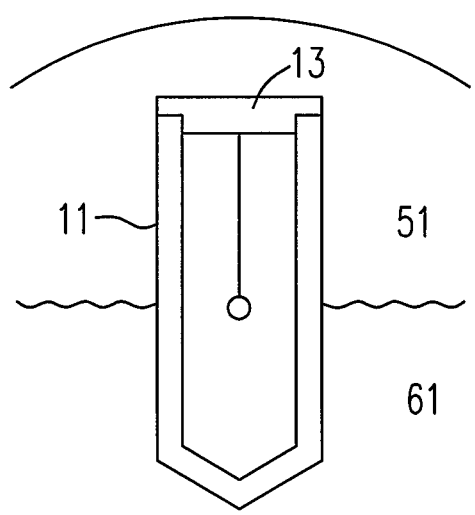
FIG. 4(b) is a schematic diagram showing the dental implant implanted in an alveolus bone according to another preferred embodiment in the present invention.

The non-contact apparatus and method for stability assessment of dental implant provided by the present invention are suitable for the one-stage dental implant system and the two-stage dental implant system. Please refer to FIG. 4(a), which shows the one-stage dental implant system, and is a schematic diagram showing the dental implant implanted in an alveolus bone according to a preferred embodiment in the present invention, wherein the opening and the cover 13 are located at the outside of a gum 51 when the dental implant 11 is implanted in the alveolus bone 61. Please refer to FIG. 4(b), which shows the two-stage dental implant system, and is a schematic diagram showing the dental implant implanted in the alveolus bone according to another preferred embodiment in the present invention, wherein the whole dental implant 11, including the opening and the cover 13 thereof, is covered in the gum 51 when implanted in the alveolus bone 61.

In conclusion, the present invention provides a non-contact apparatus and a non-contact method for stability assessment of dental implant, where a non-contact impetus is used and a special design of the dental implant is provided therein. Therefore, the stability of the dental implant can be assessed by resonance frequency measurements, and the preciseness thereof is much higher than that of X-ray gray image measurements. The present invention not only overcomes the drawbacks of the conventional resonance frequency measurements, which only can be applied in the one-stage dental implant system, but also provides more flexible alternatives for dentists and patients when doing the dental implant surgery because the present invention is suitable for both the one-stage and two-stage dental systems. Furthermore, the non-contact impetus employed in the present invention avoids the inconveniences of the conventional resonance frequency measurements, where a direct contact of external impacts is necessary, and also decreases the psychological uncomfortableness of patients. Accordingly, the present invention can effectively solve the problems and drawbacks in the prior art, and thus it fits the demand of the industry and is industrially valuable.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A non-contact apparatus for a stability assessment of a dental implant, comprising:
    a dental implant comprising:
        a root body having a cavity therein;
        an impact generating device located in the cavity, wherein the cavity has an opening; and
        a cover completely covering the opening; and
    a triggering device providing a non-contact impetus for triggering the impact generating device to cause the impact generating device to hit the root body, wherein the entire dental implant is configured to be implanted at an alveolus bone covered by a gum and the opening and the cover are configured for being located entirely in an inside of the gum when the dental implant is implanted at the alveolus bone; and wherein the dental implant is also configured to be implanted at an alveolus bone such that the opening and the cover are located in an outside of the gum when the dental implant is implanted at the alveolus bone.

2. A non-contact apparatus according to claim 1 further comprising a receiving device, wherein the non-contact impetus triggers the impact generating device to make the dental implant generate a vibration response, and the receiving device receives the vibration response.

3. A non-contact apparatus according to claim 2, wherein the receiving device is a microphone.

4. A non-contact apparatus according to claim 2 further comprising an analyzing device coupled to the receiving device and analyzing the vibration response received by the receiving device.

5. A non-contact apparatus according to claim 4, wherein the analyzing device is a computer.

6. A non-contact apparatus according to claim 1, wherein the impact generating device is a hammer having a stick, and the stick is connected to an inside surface of one of the cover and the root body.

7. A non-contact apparatus according to claim 1, wherein the impact generating device is a piece placed in the cavity.

8. A non-contact apparatus according to claim 1, wherein the impact generating device is made of a material with a magnetic permeability.

9. A non-contact apparatus according to claim 8, wherein the material is one selected from a group consisting of an iron, a cobalt, a nickel, a gadolinium and a combination thereof.

10. A non-contact apparatus according to claim 1, wherein the triggering device is a magnetic field generating device for generating one of a periodical magnetic field and an impulse magnetic field.

11. A non-contact method for a stability assessment of a dental implant, comprising steps of:
    providing the non-contact apparatus according to claim 1;
    using the triggering device to provide a non-contact impetus;
    generating a vibration response by the dental implant in response to the non-contact impetus; and
    receiving and analyzing the vibration response.

12. A non-contact method according to claim 11, wherein the impact generating device hits the root body, generating the vibration response by the dental implant in response to the non-contact impetus; and the step of receiving and analyzing the vibration response is to obtain a resonant frequency of the dental implant.

13. A non-contact method according to claim 11, wherein the method is applied in one of a one-stage dental implant system and a two-stage dental implant system.

14. A non-contact method according to claim 11, wherein the non-contact impetus is one of an impulse magnetic field and a periodical magnetic field.

* * * * *